United States Patent [19]

Quiachon et al.

[11] Patent Number: 5,749,920
[45] Date of Patent: May 12, 1998

[54] MULTICAPSULE INTRALUMINAL GRAFTING SYSTEM AND METHOD

[75] Inventors: Dinah B. Quiachon, San Jose; Alec A. Piplani, Mountain View; Larry G. Baughman, Cambell, all of Calif.

[73] Assignee: EndoVascular Technologies, Inc., Menlo Park, Calif.

[21] Appl. No.: 562,351

[22] Filed: Nov. 22, 1995

Related U.S. Application Data

[63] Continuation of Ser. No. 102,576, Aug. 5, 1993, abandoned, which is a continuation-in-part of Ser. No. 553,530, Jul. 13, 1990, Pat. No. 5,275,622, which is a continuation-in-part of Ser. No. 166,093, Mar. 9, 1988, Pat. No. 5,104,399, which is a continuation-in-part of Ser. No. 940,907, Dec. 10, 1986, Pat. No. 4,787,899, which is a continuation of Ser. No. 559,935, Dec. 9, 1983, abandoned.

[51] Int. Cl.$^6$ ............................................. A61F 2/06
[52] U.S. Cl. .................................... 623/1; 606/195
[58] Field of Search .................. 623/1, 12; 606/191–195, 606/198; 604/96, 97, 104

[56] References Cited

U.S. PATENT DOCUMENTS

| | | | |
|---|---|---|---|
| 3,657,744 | 4/1972 | Ersek | 3/1.3 |
| 4,214,587 | 7/1980 | Sakura, Jr. | 128/334 R |
| 4,560,374 | 12/1985 | Hammerslag | 604/49 |
| 4,562,596 | 1/1986 | Kornberg | 623/1 |
| 4,577,631 | 3/1986 | Kreamer | 12/334 R |
| 4,787,899 | 11/1988 | Lazarus | 623/1 |
| 5,078,726 | 1/1992 | Kreamer | 606/194 |
| 5,104,399 | 4/1992 | Lazarus | 623/1 |
| 5,108,416 | 4/1992 | Ryan et al. | 606/194 |
| 5,201,757 | 4/1993 | Heyn et al. | 606/198 |
| 5,219,355 | 6/1993 | Parodi et al. | 606/191 |
| 5,275,622 | 1/1994 | Lazarus et al. | 623/1 |

FOREIGN PATENT DOCUMENTS

| | | |
|---|---|---|
| 0 346 564 A1 | 12/1989 | European Pat. Off. . |
| 0 461 791 A1 | 12/1991 | European Pat. Off. . |
| 0 479 557 A1 | 4/1992 | European Pat. Off. . |
| 0 539 237 A1 | 4/1993 | European Pat. Off. . |
| WO 90/15582 | 12/1990 | WIPO . |
| WO95/01761 | 1/1995 | WIPO . |

OTHER PUBLICATIONS

Balko, MD et al., Journal of Surgical Research (1986); pp. 40:305–309, "Transfemoral Placement of Intraluminal Polyurethane Prosthesis for Abdominal Aortic Aneurysm".

Lawrence, Jr. MD et al., Radiology (1987); pp. 163:357–360, "Percutaneous Endovascular Graft: Experimental Evaluation".

Yoshioka et al., AJR (Oct. 1988); pp. 151:673–676, "Self-Expanding Endovascular Graft: An Experimental Study In Dogs".

(List continued on next page.)

*Primary Examiner*—Michael J. Milano
*Attorney, Agent, or Firm*—Fulwider Patton Lee & Utecht, LLP

[57] ABSTRACT

An intraluminal grafting system having a balloon catheter assembly, a capsule catheter assembly and capsule jacket assembly is used for deploying a graft having attachment means in the vessel of an animal body. The system contains a proximal capsule means and a distal capsule means, wherein the graft is disposed within the two capsule means and a removable sheath covers the graft and capsule means. The graft is comprised of a tubular member having superior and inferior ends, having attachment means with wall engaging members secured thereto. The balloon catheter is disposed within the capsule catheter to provide relative movement between the balloon catheter and the capsule catheter, whereby the graft can be removed from the capsule means. The balloon is inflated to firmly implant the graft and attachment means within the vessel. The graft and attachment means remain in the vessel after the intraluminal grafting system is withdrawn.

7 Claims, 11 Drawing Sheets

OTHER PUBLICATIONS

Mirich, MD et al., Radiology (1989); pp. 170:1033–1037, "Percutaneously Placed Endovascular Grafts for Aortic Aneurysms: Feasibility Study".

Parodi, MD, et al., Ann Vasc Surg (1991); pp. 5:491–499, "Transfemoral Intraluminal Graft Implantation for Abdominal Aortic Aneurysms".

Claude et al., Radiology (1992); pp. 184:185–190, "Intraluminal Bypass of Abdominal Aortic Aneurysm: Feasibility Study".

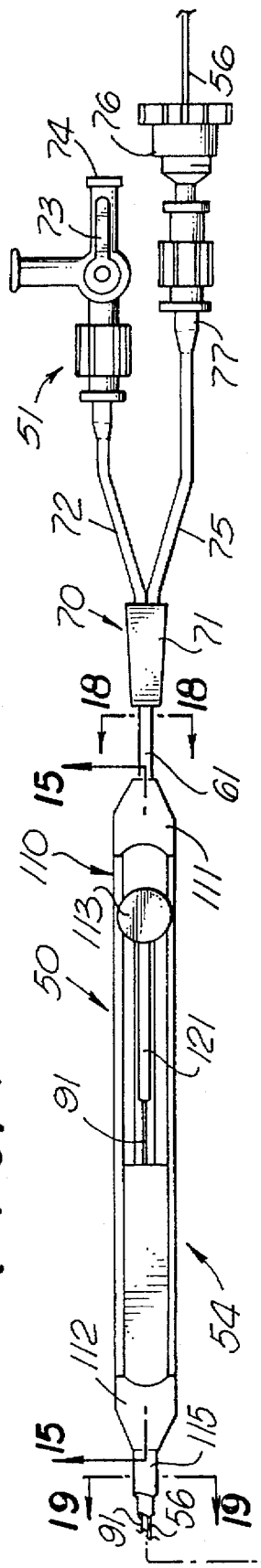
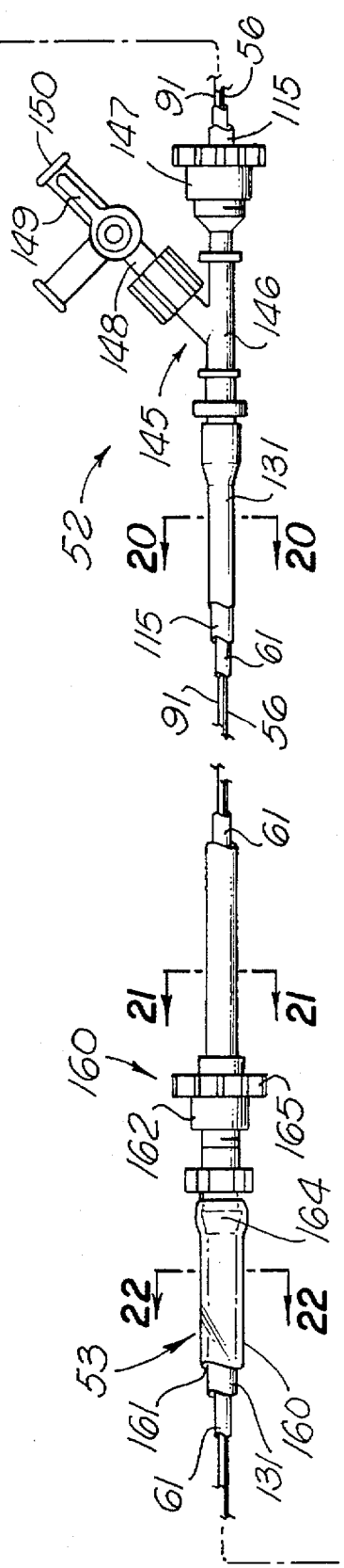
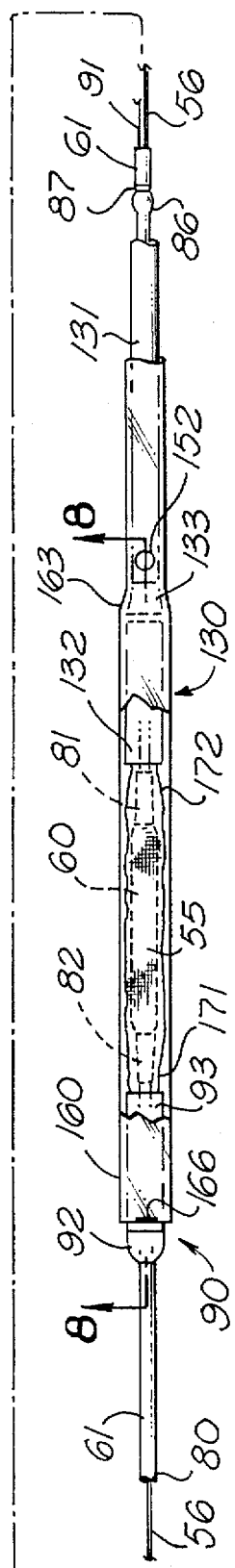
FIG. 1

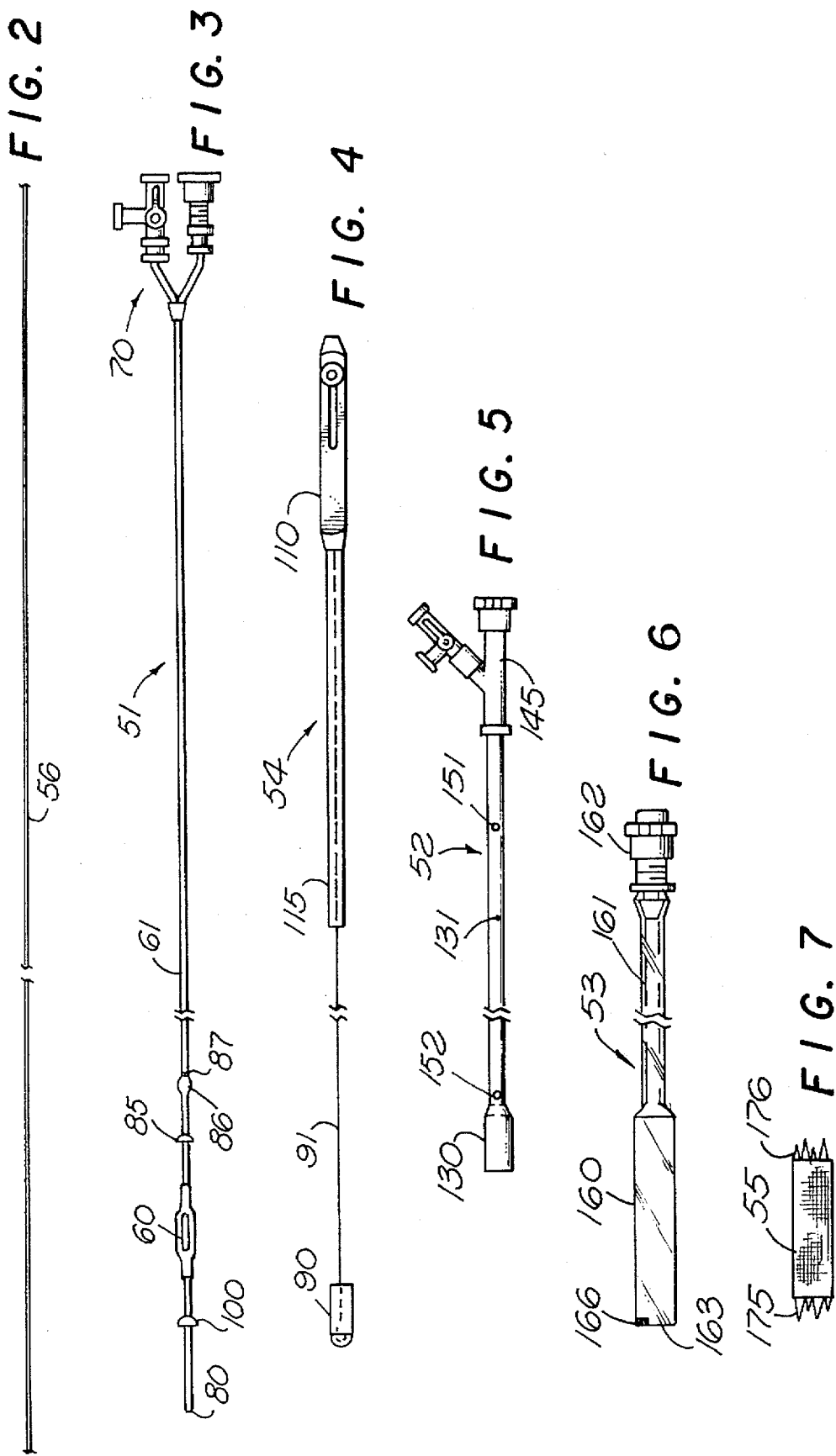

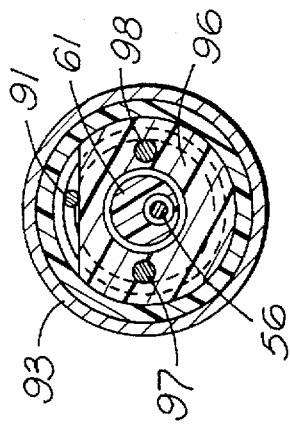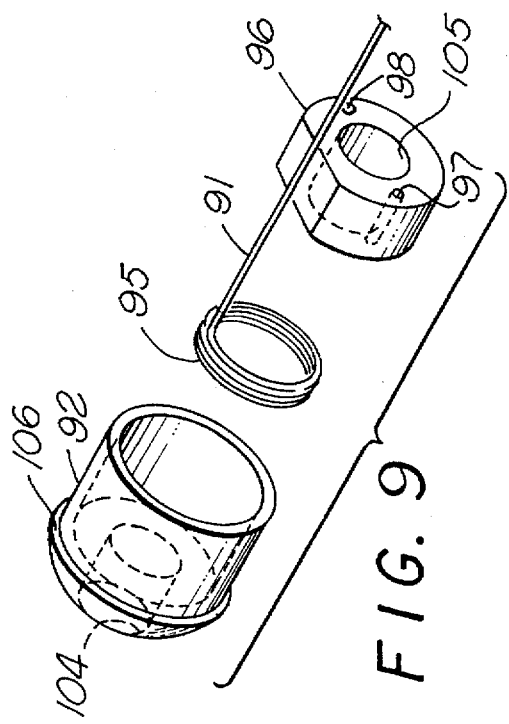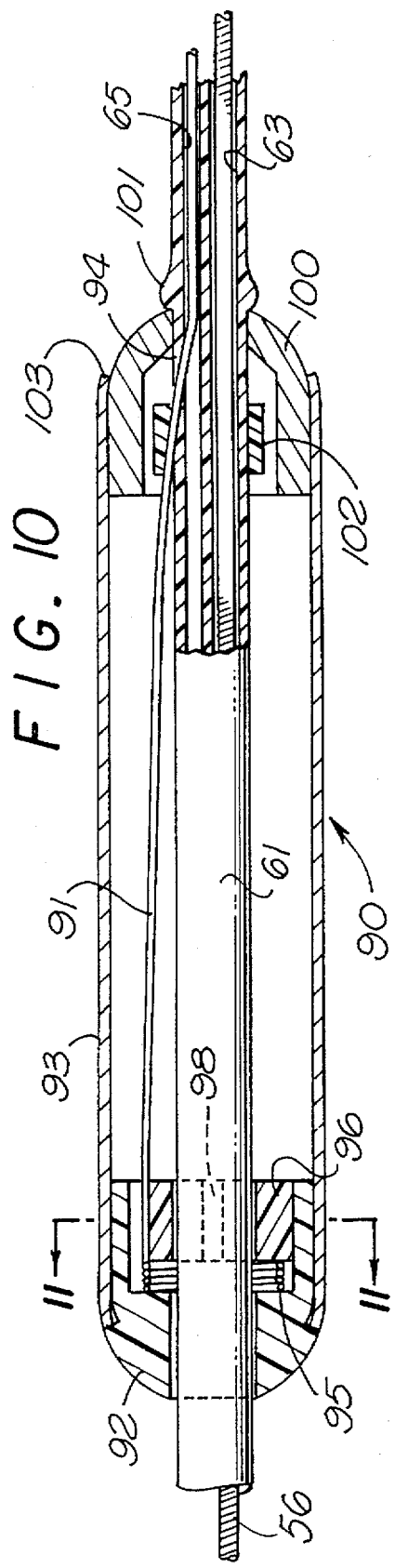

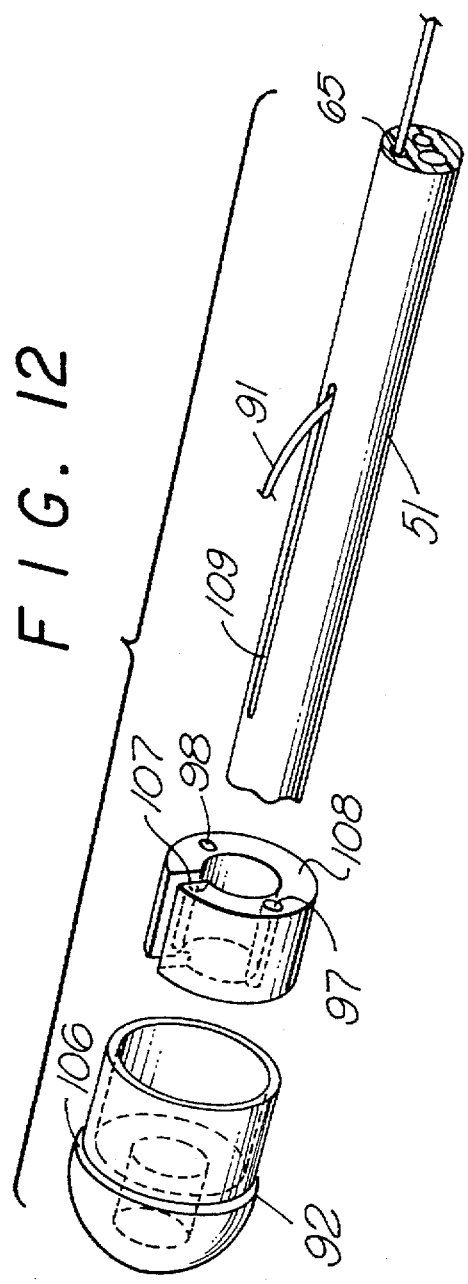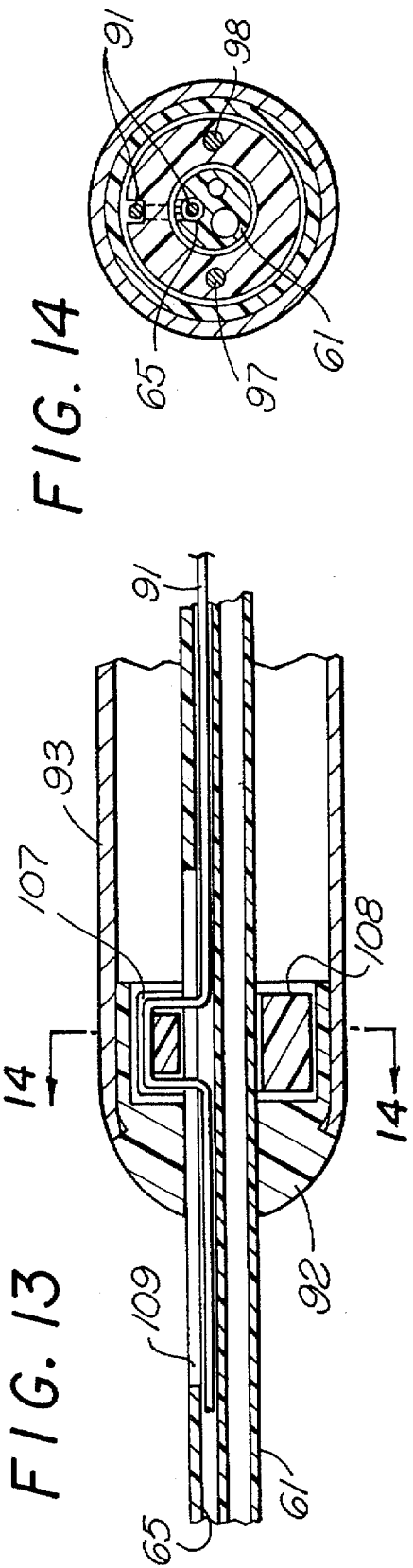

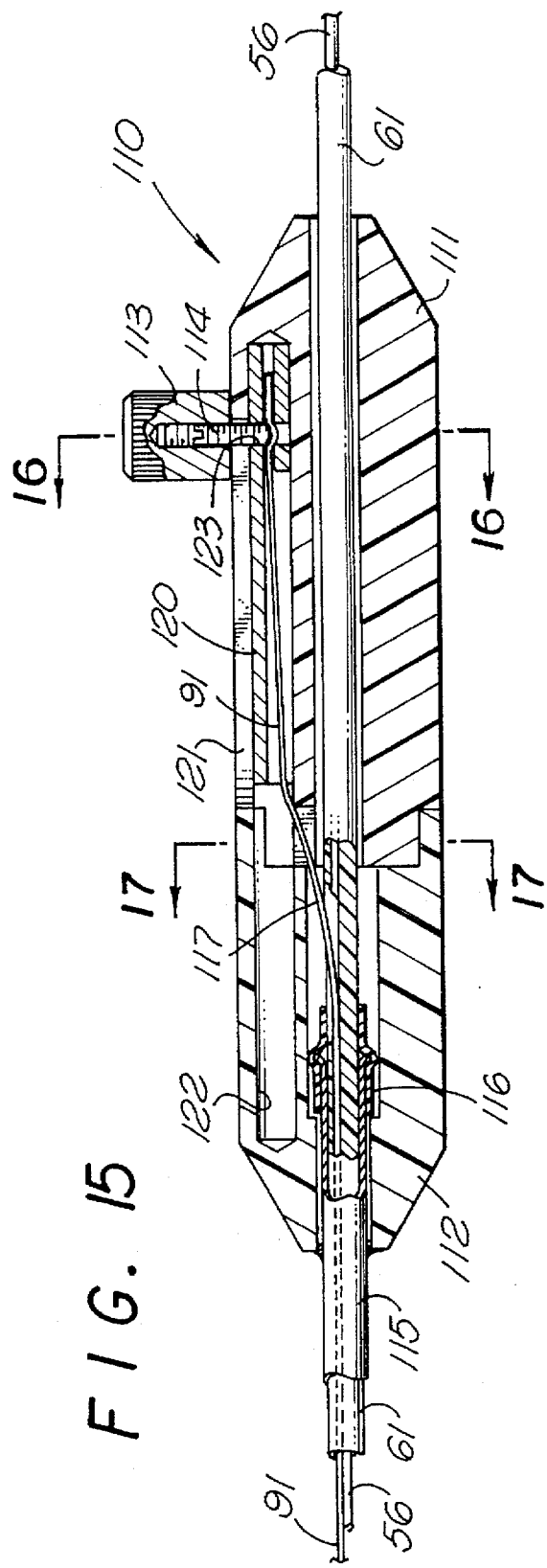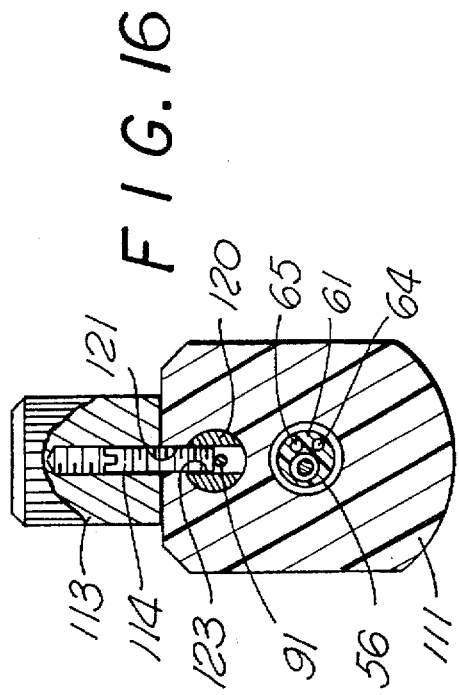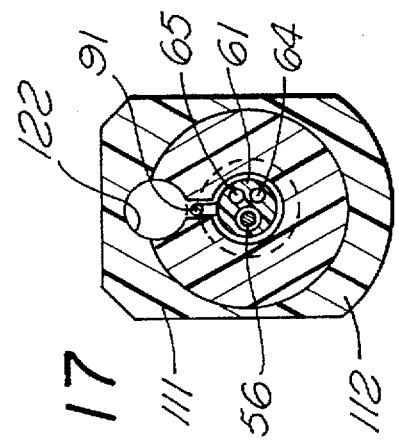

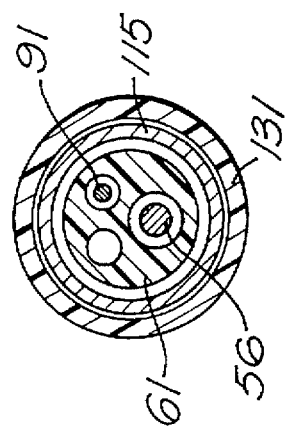
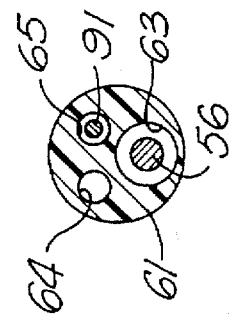
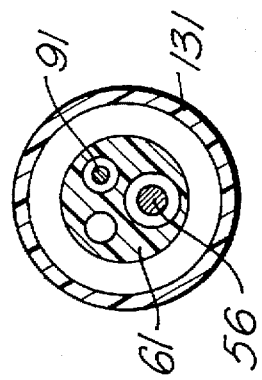
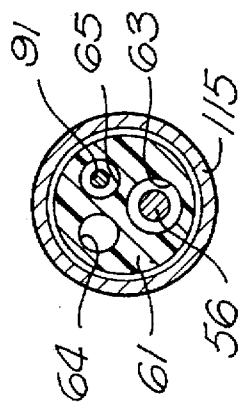
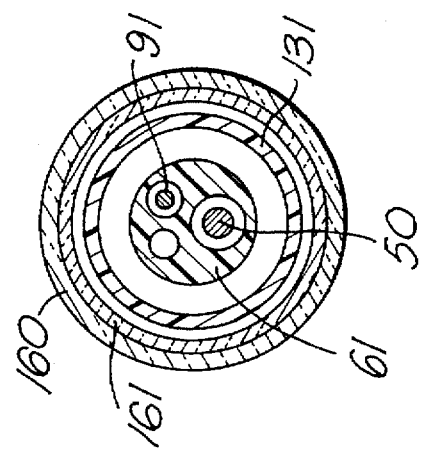

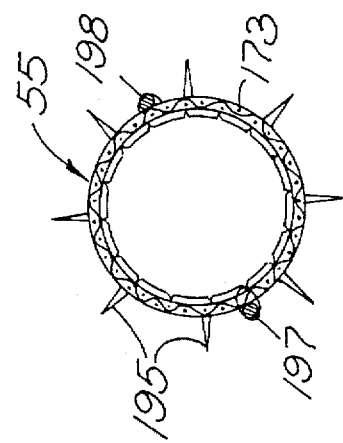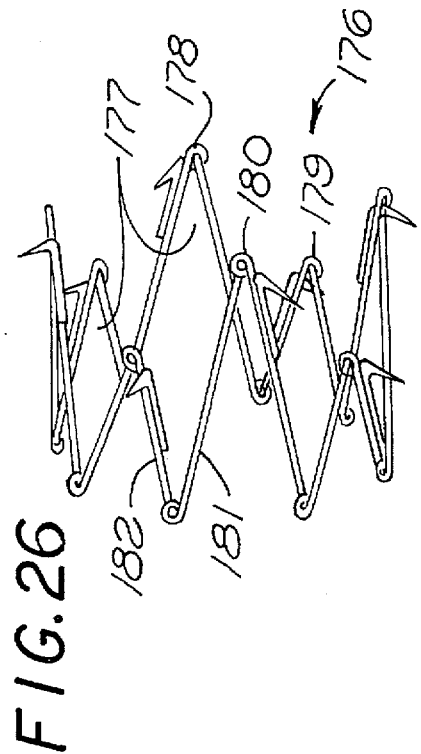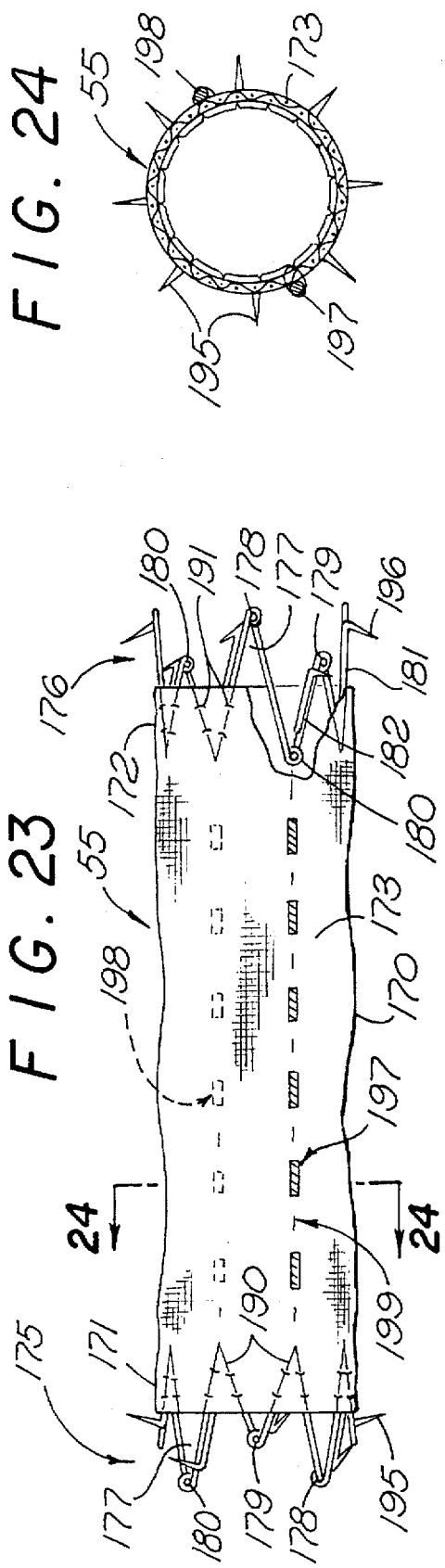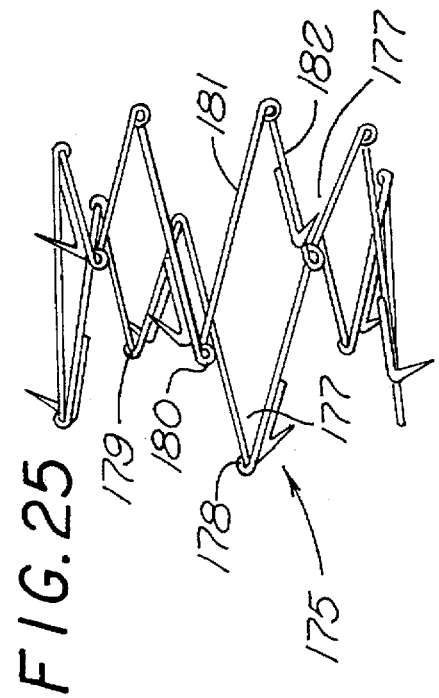

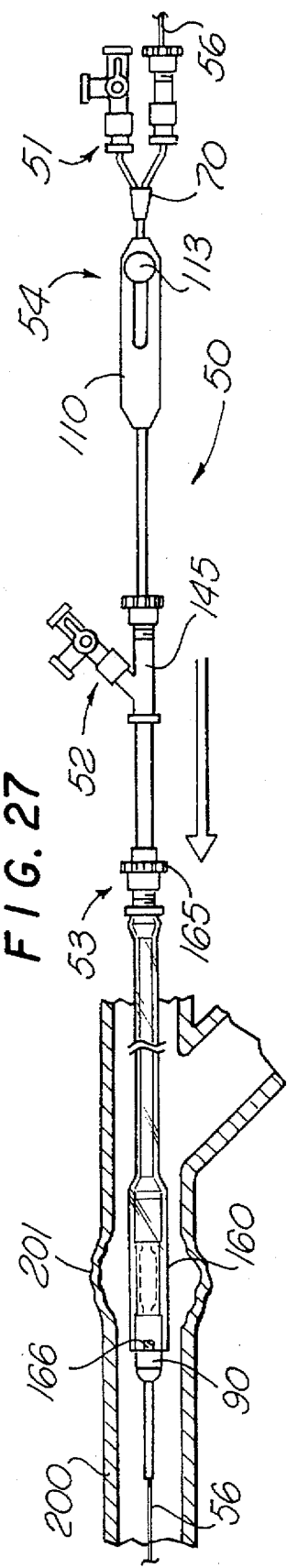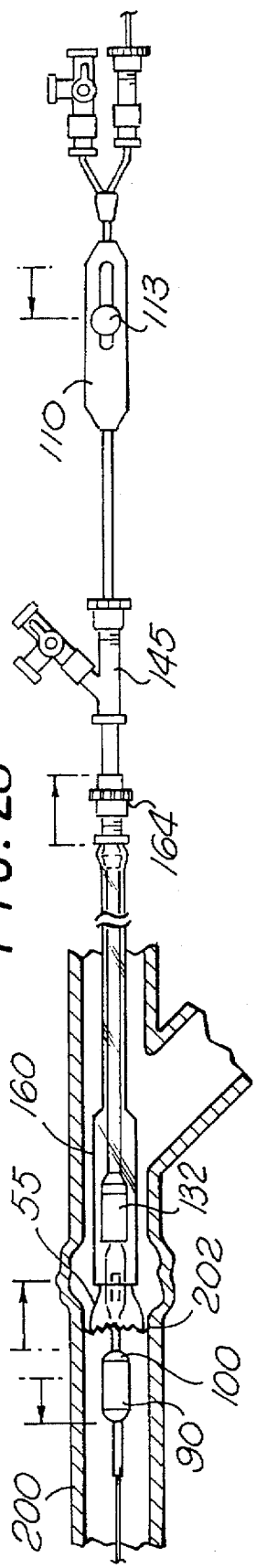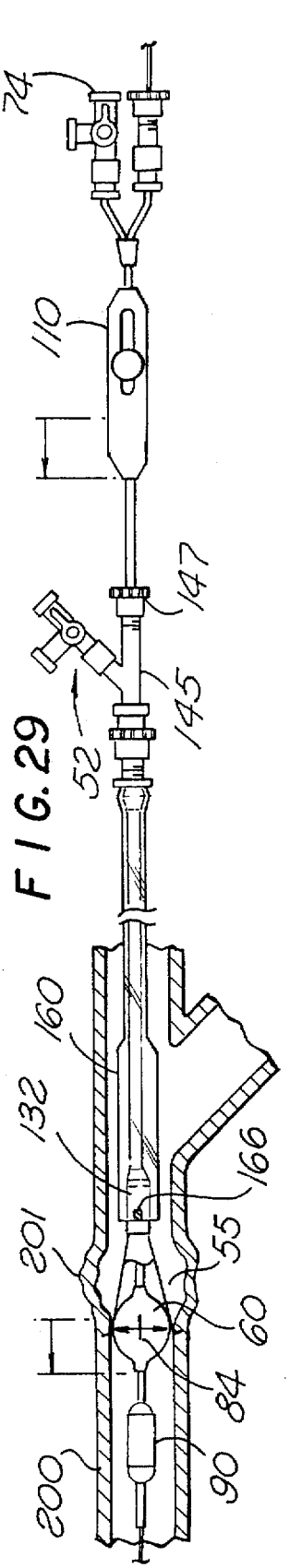

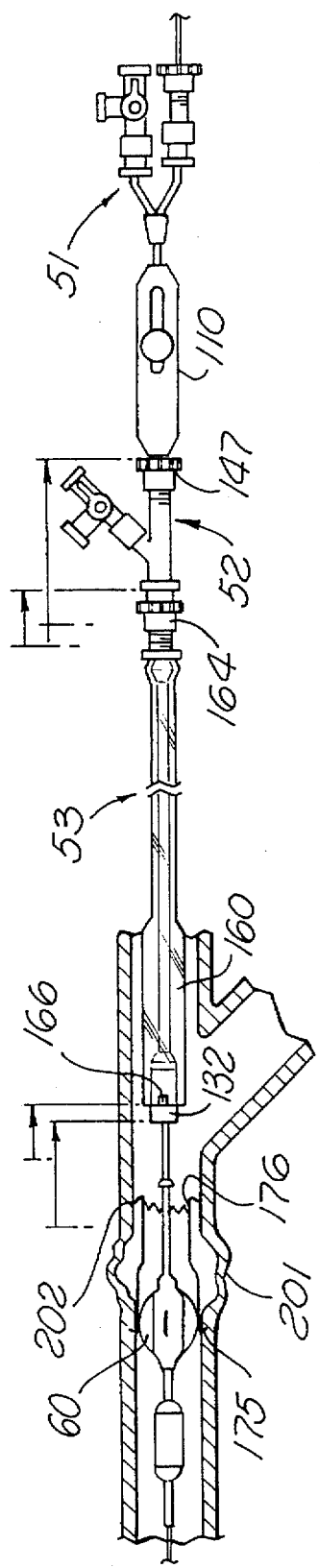
F I G. 30
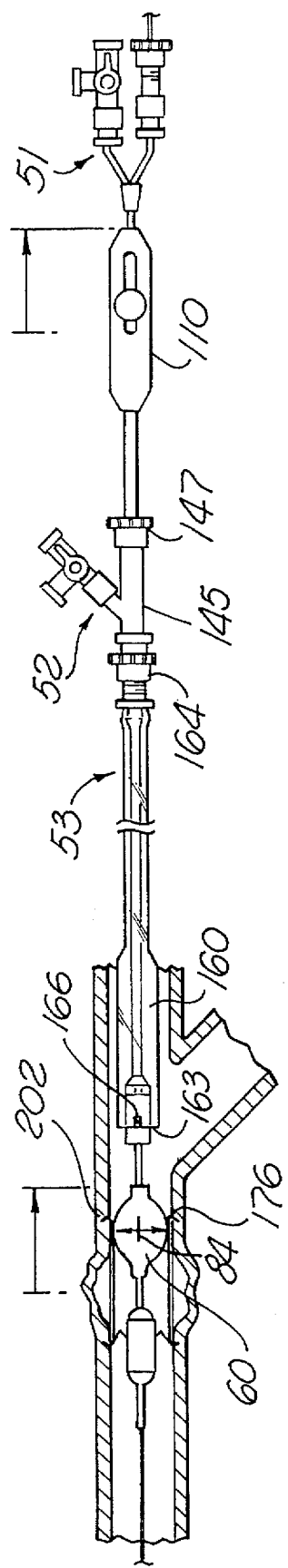
F I G. 31

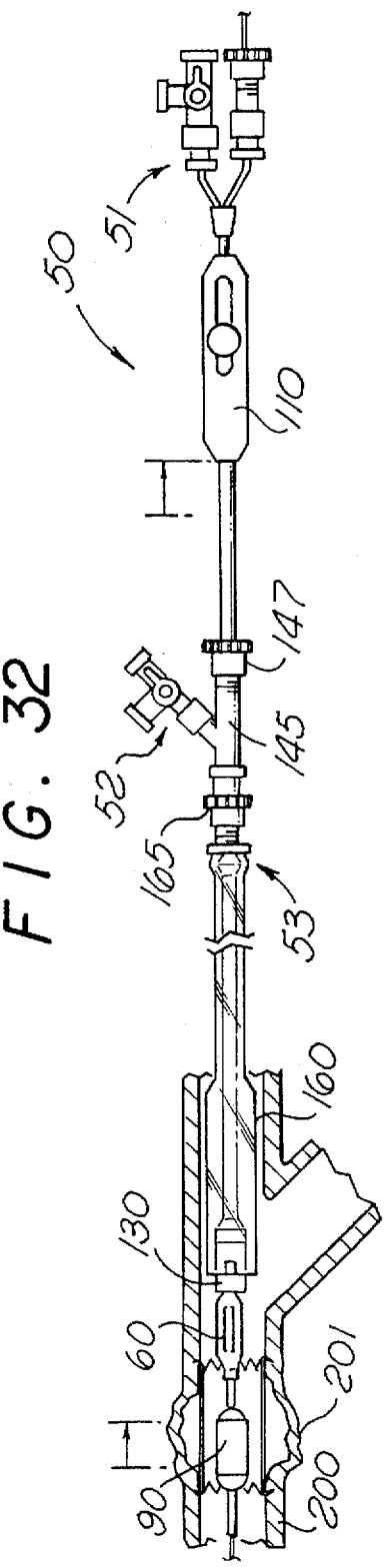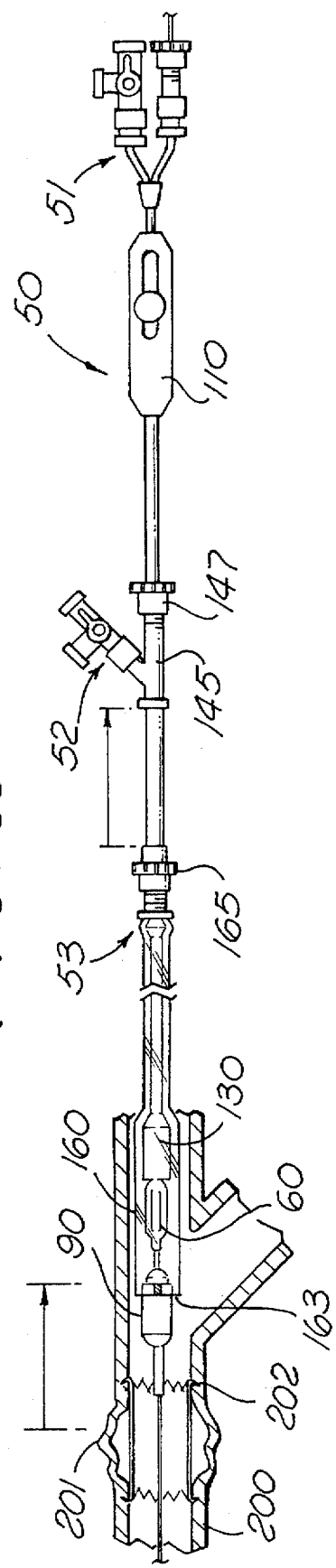

MULTICAPSULE INTRALUMINAL GRAFTING SYSTEM AND METHOD

This application is a continuation of application Ser. No. 08/102,576 filed Aug. 5, 1993 now abandoned, which is a continuation-in-part of application Ser. No. 07/553,530 filed on Jul. 13, 1990, now U.S. Pat. No. 5,275,622, which is a continuation-in-part of application Ser. No. 07/166,093 filed on Mar. 9, 1988, now U.S. Pat. No. 5,104,399, which is a continuation-in-part of application Ser. No. 07/940,907 filed on Dec. 10, 1986, now U.S. Pat. No. 4,787,899 which is a continuation of application Ser. No. 06/559,935 filed on. Dec. 9, 1983, now abandoned. The contents of each of these applications are hereby incorporated by reference.

BACKGROUND OF THE INVENTION

This invention relates to a system for emplacing a prosthesis and, more particularly, to a catheter system for placement of a graft having attachment means within a corporeal lumen.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and in turn may be life-threatening. In some cases, the damaged lumen is repairable only with the use of prosthesis such as an artificial vessel or graft.

For repair of vital vessels such as the aorta, surgical repair is significantly life-threatening. Surgical techniques known in the art involve major surgery in which a graft resembling the natural vessel is spliced into the diseased or obstructed section of the natural vessel. Known procedures include surgically removing or bypassing the damaged or diseased portion of the vessel and inserting an artificial or donor graft inserted and stitched to the ends of the vessel which were created by the removal of the diseased portion.

It is known within the art to provide a prothesis for intraluminal repair of a vessel, such as an abdominal aorta having an aneurysm. The art has taught to provide a prothesis positioned in a vessel then securing the prothesis within the vessel with hooks or staples that are mechanically extended by the user. The early prior art devices were large in diameter, mechanically complex and in turn were susceptible to mechanical failure. Prior intraluminal grafting systems have embodied capsule catheters or balloon catheters, but were relatively stiff and of a relatively high profile. Similarly, the prior art systems were configured in such a way that the graft was relatively difficult to deploy the prothesis. In addition, prior systems having capsule catheter means were usually configured such that the prothesis was disposed within a unitary capsule.

In recent years, several devices have been developed to attempt to treat an aortic aneurysm through intraluminal repair. For example, U.S. Pat. No. 4,140,126 (Feb. 20, 1979), Choudhury, discloses a method and article for performing an aneurysm repair, wherein a prosthetic graft is utilized to replace the damaged segment of the blood vessel. A plurality of radially spaced anchoring pins are located adjacent each end of the graft and provide means for securing the graft to the wall of the vessel. Means is provided for moving the graft within the vessel and permanently anchoring the graft to the wall of the vessel.

U.S. Pat. No. 4,562,596 (Jan. 7, 1986), Kornberg, discloses a bifurcated aortic graft constructed for intraluminal insertion having a plurality of struts having angled hooks with barbs at their superior ends. Means for inserting the graft and implanting the hooks into the vessel lumen is also disclosed.

U.S. Pat. No. 4,787,899 (Nov. 29, 1988), Lazarus, discloses an intraluminal grafting system including a hollow graft having an attachment means located at one end of the graft. The system includes positioning means for moving the graft within the vessel, the positioning means having a capsule positioned at one end for covering the graft attachment means. The disclosed positioning means further includes an inflatable member for securing the attachment means within the lumen.

EPO Pub. No. 0 461 791 A1 (Dec. 18, 1991), Barone et al. discloses an aortic graft and apparatus for repairing an aneurism. The disclosed system includes a tube graft secured within the aorta and an attachment means at each end of the graft. Intraluminal delivery is accomplished using a catheter having a balloon for expanding and securing the attachment means. The graft and attachment means are preferably enclosed by a sheath which covers the entire graft and attachment means.

EPO Pub. No. 0 466 518 A3 (Jan. 15, 1992), Lazarus et al., discloses an intraluminal grafting system including a catheter having a capsule formed of a helical wrap of metal ribbon. A tubular graft having attachment means at both ends is removably disposed within the capsule. Means is provided for moving the graft from the capsule, and an inflatable member is provided for securing the attachment means within a vessel lumen.

U.S. Patent No. 5,104,399 (Apr. 14, 1992), Lazarus, discloses an intraluminal grafting system including a tubular graft having attachment means positioned at both ends. The system includes a positioning means for transporting the graft through a vessel lumen and for deploying the graft within the lumen. The positioning means includes an inflatable member, a capsule and means for removing the graft from the capsule. The capsule is disclosed as a rigid cylindrical member covering the entire graft.

EPO Pub. No. 0 508 473 A2 (Oct. 14, 1992), Piplani et al., discloses an intraluminal grafting system including a catheter having a capsule formed of a helical wrap of metal ribbon. A bifurcated graft having attachment means is removably disposed within the capsule. Means is provided for moving the graft from the capsule, and an inflatable member is provided for securing the attachment means within a vessel lumen.

The foregoing patents and publications are incorporated herein by reference.

To provide consistency with the common usage of terms used in the medical surgical arts in the United States, the terms "proximal, distal, inferior and superior" are used with a certain regularity within the present specification. Proximal refers to parts of the system, such as catheters, capsules and wires, which are closest to the user and closest to the portion of the system outside or exterior of the patient. Distal refers to the point farthest from the user and typically most interior to the corporeal lumen. The term superior refers to a location situated above and is used herein in description of the graft and attachment means. Inferior refers to the point situated below and again is used herein with the graft and attachment means. Thus, for applications in the abdominal aorta which use a femoral approach, the superior end of the graft resides within the most distal portion of the balloon catheter. Likewise, the inferior end of the graft resides within the proximal capsule which is on the most distal portion of the capsule catheter.

SUMMARY OF THE INVENTION

In general, it is an object of the present invention to provide an intraluminal grafting system and method which overcome the disadvantages of the prior art systems.

The present system has several advantages over prior art systems. For example, the over the wire configuration of the balloon catheter enables traversing the aneurysm with a guidewire. Using a guidewire in this manner minimizes the risk of dislodging thrombus in the aneurysm, since the placement means follows the guidewire thereby preventing the distal tip from contacting the vessel wall. In addition, using a guidewire allows for traversing more difficult anatomy. Also, the guide wire lumen may function as a through lumen for real time angiograms during the emplacement procedure or to insert intravascular probes such as intravascular ultrasound systems.

As another advantage, the smaller diameter and lower profile of the capsule assemblies of the present invention permit use of the invention in a larger patient population because the variances in iliac vessel diameter. Similarly, the smaller device diameter relative to the iliac diameter may allow for easier navigation inside the corporeal lumen especially with more difficult anatomy. Likewise, the two capsule segments of the present invention permit a wider range of graft lengths than available with a single capsule design. The single capsule systems also require capsules slightly longer than the graft, which imposes certain manufacturing and deployment problems. Moreover, the shorter capsule segments provide a more flexible device, thereby allowing traversing more difficult anatomy.

The present invention comprises an intraluminal placement means for securing a prothesis within or between vessels or corporeal lumens of an animal, such as a human. The preferred embodiment of the placement means is configured for introducing a graft into a corporeal lumen and positioning the graft in the area of the aortic bifrucation. The placement means includes a balloon catheter, a capsule catheter and a capsule jacket. In the preferred embodiment, the balloon catheter and capsule catheter include capsule means for retaining the graft, including a proximal capsule means and a distal capsule means. The capsule means are movable relative to each other to allow the graft to be emplaced at the desired location in the corporeal lumen.

Preferably, the placement means includes a balloon catheter having a multilumen hollow tube or shaft having a proximal end provided with means for accepting a guide wire and with means for inflating a balloon or similar inflatable member. The balloon catheter shaft is of sufficient length that the proximal end remains exterior the corporeal lumen while the distal end of the balloon catheter shaft may be positioned proximate the portion of the corporeal lumen to be repaired. The balloon catheter further has means for inflating and deflating the balloon. In addition, the balloon catheter is coupled to control means and a distal capsule for retaining and releasing the superior end of the graft. In the preferred embodiment, the control means includes a control wire and handle mechanism which provides movement of the distal capsule relative to the balloon catheter shaft.

The placement means also includes a capsule catheter shaped and sized for positioning within the corporeal lumen. The capsule catheter comprises a hollow tube or shaft slidably mounted on the balloon catheter shaft, having a proximal end exterior the corporeal lumen for manipulation by the user. The capsule catheter includes a proximal capsule secured to the distal end of the capsule catheter shaft for retaining the inferior end of the graft. The placement means is configured to provide relative movement between the proximal capsule of the capsule catheter and the distal capsule of the balloon catheter for removing the graft from the capsule means and for subsequently urging the attachment means into engagement with the wall of the corporeal lumen.

The placement means further includes a capsule jacket for providing a smooth transition between the parts of the balloon catheter and capsule catheter. The capsule jacket comprises a double walled jacket or sheath configured coaxially with the balloon catheter and capsule catheter, having a proximal end exterior the corporeal lumen for manipulation by the user. The distal end of the capsule jacket flares outwardly to a size which is slidably retained over the distal capsule when the placement means in deployed into the corporeal lumen.

The present invention includes a prosthesis or graft for intraluminal placement in a fluid conducting corporeal lumen. For most applications the prothesis is a hollow graft of preselected cross-section and length. The graft is deformable to conform substantially to the interior surface of the corporeal lumen or other body part to be repaired. Preferably, the graft is made of a material suitable for permanent placement in the body such as polytetrafluroethylene or a polyester. During emplacement, the superior and inferior ends of the graft are positioned within the corporeal lumen and the graft is configured such that the graft traverses the diseased or damaged portion of the vessel. To anchor the graft to the wall of the corporeal lumen, attachment means are secured to the superior and inferior ends of the graft.

The preferred attachment means has wall engaging members. The wall engaging members of the superior attachment means are angled toward the inferior end of the graft. Similarly, the wall engaging members of the inferior attachment means are angled slightly toward the superior end of the graft. The wall engaging members of both attachment means have sharp tips for engaging the corporeal lumen wall. The preferred attachment means are formed into a V-shaped lattice or framework. The frame of the attachment means allows for elastic radial deformation resulting in a spring-like effect when a compressed attachment means is allowed to expand as the graft is released from the capsule means. In addition, radiopaque markers are secured to the longitudinal axis of the graft to facilitate orientation of the graft using fluoroscopy or x-ray techniques.

Deployment of the graft comprises a series of steps which begins with introducing the placement means into the corporeal lumen using well known surgical techniques. As a single system, the balloon catheter, capsule catheter and capsule jacket are manipulated to position the capsule means containing the graft and attachment means to a desired location within the corporeal lumen. Once the graft is in the desired location, the capsule jacket is withdrawn to expose the distal capsule and a portion of the graft. The distal capsule is then moved relative to the balloon catheter shaft and capsule catheter to expose the superior attachment means.

After the superior portion of the graft is removed from the capsule means, the inflatable member is moved to within the circumference of the superior attachment means and inflated to urge wall engaging members into the wall of the corporeal lumen. The capsule jacket and capsule catheter are then moved relative to the graft and balloon catheter shaft to expose the inferior attachment means. The balloon catheter shaft is then moved to position the inflatable member proximate the inferior attachment means. The inflatable member is then expanded to seat the wall engaging members of the inferior attachment means. The placement means is then removed from the corporeal lumen.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a top plan view of an intraluminal grafting apparatus and system incorporating the present invention.

FIG. 2 is a top plan view of a guidewire to be used with the endovascular grafting system of the present invention.

FIG. 3 is a top plan view of the balloon catheter of the present invention.

FIG. 4 is a top plan view of the distal cap, control wire, guiding tube and control wire handle assembly of the present invention.

FIG. 5 is a top plan view of the proximal capsule and capsule catheter assembly of the present invention.

FIG. 6 is a top plan view of the capsule jacket assembly of the present invention.

FIG. 7 is a top plan view of a graft for use with the system incorporating the present invention.

FIG. 9 is an enlarged perspective view showing an embodiment of the distal capsule, distal end of the control wire and distal cap insert.

FIG. 10 is an enlarged cross-sectional view of one embodiment of the distal capsule means of the balloon catheter.

FIG. 11 is a cross-sectional view taken along the line 11—11 of FIG. 10.

FIG. 12 is an enlarged perspective view showing an embodiment of the distal capsule, distal end of the control wire and distal cap insert.

FIG. 13 is an enlarged cross-sectional view of an embodiment of the distal capsule means of the balloon catheter.

FIG. 14 is a cross-sectional view taken along the line 14—14 of FIG. 13.

FIG. 15 is a partial cross-sectional view of the control wire and control handle mechanism taken along the line 15—15 of FIG. 1.

FIG. 16 is a cross-sectional view taken along the line 16—16 of FIG. 15.

FIG. 17 is a cross-sectional view taken along the line 17—17 of FIG. 15.

FIG. 18 is a cross-sectional view taken along the line 18—18 of FIG. 1.

FIG. 19 is a cross-sectional view taken along the line 19—19 of FIG. 1.

FIG. 20 is a cross-sectional view taken along the line 20—20 of FIG. 1.

FIG. 21 is a cross-sectional view taken along the line 21—21 of FIG. 1.

FIG. 22 is a cross-sectional view taken along the line 22—22 of FIG. 1.

FIG. 23 is a partial cross-sectional view of the graft and attachment means of the present invention.

FIG. 24 is a cross-sectional view taken along the line 24—24 of FIG. 23.

FIG. 25 is an enlarged perspective view showing a superior attachment means.

FIG. 26 is an enlarged perspective view showing an inferior attachment means.

FIG. 27 is a partial cross-sectional view of the intraluminal grafting system shown positioned within the corporeal lumen.

FIG. 28 is a partial cross-sectional view of the intraluminal grafting system, wherein the distal capsule has been removed from the superior end of the graft.

FIG. 29 is a partial cross-section view of the intraluminal grafting system, wherein the inflatable member has been expanded to seat the attachment means of the graft.

FIG. 30 is a partial cross-sectional view of the intraluminal grafting system, wherein the capsule jacket and capsule catheter have been withdrawn from the inferior end of the graft.

FIG. 31 is a partial cross-sectional view of the intraluminal grafting system, wherein the inflatable member has been positioned and inflated to seat the inferior attachment means.

FIG. 32 is a partial cross-sectional view of the intraluminal grafting system, wherein the inflatable member has been moved proximate the proximal capsule.

FIG. 33 is a partial cross-sectional view of the intraluminal grafting system, wherein the balloon catheter, capsule catheter and capsule jacket have been placed in a position for withdrawal from the corporeal lumen.

DESCRIPTION OF THE PREFERRED EMBODIMENTS

Figure 8:
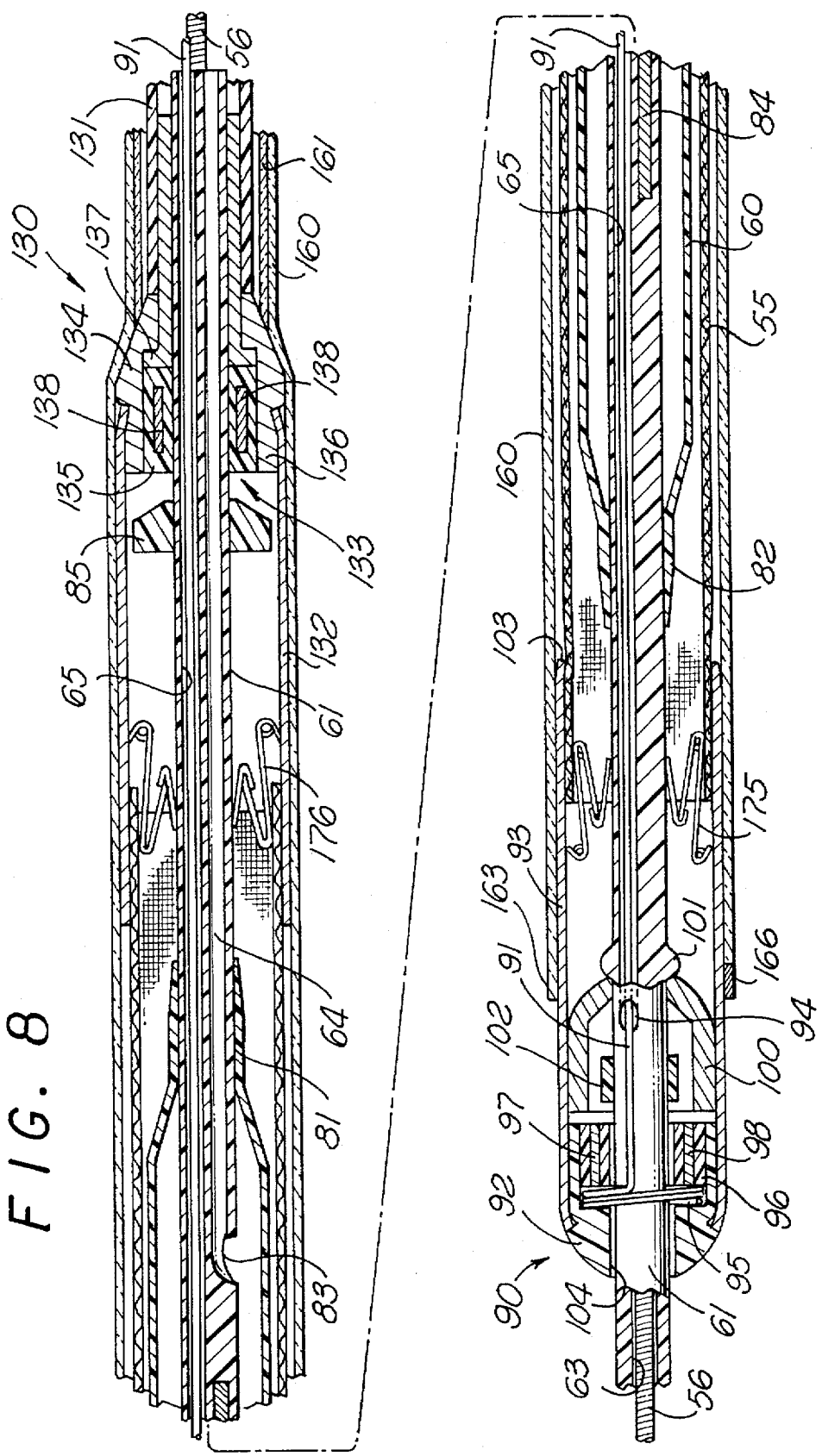
FIG. 8 is a partial cross-sectional view of the distal end of the balloon catheter, capsule catheter and capsule jacket assemblies taken along the line 8—8 of FIG. 1.

As shown in the drawings and for purposes of illustration, the invention is embodied in an intraluminal grafting system of the type having a balloon catheter, a capsule catheter, and a protective sleeve or capsule jacket. One of the novel features of the present system is the use of a proximal capsule and a distal capsule to cover the inferior and superior ends of a graft to be implanted in the vessel. This feature provides the capability of deploying the interior end of the graft before the superior end or visa versa. Another novel feature of the present invention is the use of a sleeve or capsule jacket to create a smooth transition between the proximal capsule and the distal capsule. The uniqueness of the system is accentuated by the control wire and associated handle which provide relative movement between the distal capsule and the balloon catheter.

In the present system, the graft is comprised of a monoluminal tubular member having superior and inferior extremities. Attachment means are secured to the superior and inferior ends of the tubular member. The attachment means are provided with lumen piercing means which are covered by the proximal and distal capsule assemblies. The balloon catheter, capsule catheter and capsule jacket are configured coaxially so that relative movement between them provides for deployment of the graft. The inflatable member of the balloon catheter is used to firmly implant the graft in the lumen.

In more detail, the intraluminal grafting system 50 is shown in FIGS. 1–7. As shown in FIG. 1, the system includes a balloon catheter assembly 51, which is coaxially disposed within capsule catheter assembly 52, which is coaxially disposed within capsule jacket assembly 53. The capsule catheter and a distal capsule catheter assembly 90 are used to contain the graft 55. A control wire assembly 54 is coaxially disposed within a lumen of the balloon catheter assembly and configured to move the distal capsule assembly in relation to the other system components. In the preferred embodiment, the system is used as an over-the-wire device, such that the balloon catheter is further configured with a lumen for a guide wire 56. It is contemplated, however, that the system can also be used with well known fixed wire delivery system configurations.

As shown in FIGS. 1 and 3, the intraluminal grafting system 50 also includes a balloon catheter assembly 51 which consists of an inflatable member or balloon 60 secured to a flexible elongate element or balloon catheter shaft 61. As shown in FIG. 18, the balloon catheter shaft is preferably configured with three lumens; however, the balloon catheter may be configured with a single, dual or similar multilumen shaft. A guide wire lumen 63 extends the length of the balloon catheter shaft. Similarly, a balloon inflation lumen 64 extends from the proximal end 70 of the balloon catheter to the inflatable member 60, wherein an inflation port 83, FIG. 8, is provided to allow inflation fluid to enter and exit the inflatable member. The third lumen 65 is provided for the control wire assembly 54.

The flexible elongate element or balloon catheter shaft 61 is preferably formed of a material suitable for intraluminal use, such as irradiated polyethylene tubing. The three lumen balloon catheter shaft is preferably extruded to an outside diameter of 0.08 inches (2.03 mm). The guide wire lumen 63 has an inner diameter of 0.042 inches (1.07 mm). The inflation lumen 64 and the control wire lumen 65 have identical inner diameters of 0.022 inches (0.56 mm). However, the lumen inside diameter may range from 0.015 to 0.06 inches (0.381–1.52 mm) and the outside diameter may range from 0.035 to 0.1 inches (0.889–2.54 mm) for a multilumen balloon catheter shaft. The balloon catheter may vary in length to suit the application, for example, from fifty to one hundred-fifty centimeters.

Referring to FIG. 1, the proximal extremity 70 of the balloon catheter shaft 61 is secured to a splitting adapter 71 which splits the guide wire lumen 63 from inflation lumen 64. The side arm 72 of the adapter 71 has a stop cock 73 mounted at its proximal end which is movable between open and closed positions. The stop cock is provided with a Luer fitting 74 which is adapted to be secured to a syringe for injecting inflation fluid. The side arm 75 of the adapter 71 is connected to female Luer fitting 77 for distal tip injection and to a Touhy Borst adapter 76 which is configured to removably and slidably receive the guide wire 56.

The inflatable member or balloon 60 is preferably secured twelve centimeters from the distal extremity 80 of the balloon catheter shaft 61. The balloon is positioned proximal of the distal capsule assembly 90 and the superior end of the graft 55. For shorter grafts of four to seven centimeters in length, the inflatable member may be positioned distal of the distal capsule assembly. The balloon is formed of suitable material such as polyethylene. The balloon can vary in diameter from twelve to forty-five millimeters in diameter and can have a wall thickness ranging from 0.001 to 0.005 inches (0.0254–0.127 mm). The polyethylene utilized for the balloon is irradiated to achieve an appropriate balloon size. The preferred balloon made in accordance with the present invention has an outside diameter of twenty-four millimeters, a diameter equal to the inner diameter of the graft, and had a wall thickness of approximately 0.003 inches (0.076 mm). In addition, the balloon is pleated along its axis for a low profile which facilitates its introduction into a corporeal lumen of a patient as hereinafter described. Further, the deflated balloon is heated to provide it with a memory of its low profile configuration.

Balloon catheter shaft 61 is provided with an inflation lumen 64 which is in fluid communication with the inflation port 74. The inflation lumen is used to inflate and deflate the balloon 60 by introducing and withdrawing a gas or liquid through the inflation port. The balloon is secured approximately twelve centimeters from the distal extremity 80 of the balloon catheter shaft. The balloon proximal stem 81 and balloon distal stem 82 are heat sealed to the balloon catheter shaft to form a fluid tight seal. The length of the proximal stem may vary from 0.5 to 5.0 centimeters so that the balloon will span the distance between the inferior and superior attachment means of the graft 55.

The balloon catheter shaft 61 has an inflation port 83 located approximately ten millimeters distal the balloon proximal stem 81. In addition, a radiopaque marker 84 is embedded in the balloon catheter shaft approximately two millimeters distal the balloon inflation port. Preferably, the radiopaque marker is a platinum or tungsten coil one centimeter long with an outer diameter of 0.02 inches (0.508 mm) and is located proximate the center of the balloon 60. It should be appreciated that although a separate inflatable member has been described in the drawing, an integral coaxial inflatable member may be provided which is formed of the same tubing from which the balloon catheter shaft is made. This can be readily accomplished, as is well known to those skilled in the art, by using an additional radiation dose for the balloon region of the shaft.

As shown in FIGS. 2 and 8, a pusher button 85 is slidably mounted on the balloon catheter shaft 61 and is located proximal the balloon proximal stem 81, for example, a distance of five to eight centimeters. The pusher button is retained from moving proximal on the shaft by an annular bulb 86 which is formed by localized heating of the shaft. A radiological marker band 87 is placed on the shaft just proximal the annular bulb. The pusher button is preferably cylindrical having a preferred outside diameter of 0.22 inches (5.588 mm), ranging from 0.15 to 0.25 inches (3.81–6.35 mm). The pusher button is formed of a suitable material such as 300 series stainless steel to achieve radiopacity.

The balloon itself can also be observed under x-rays because the blood in the patient's vessel is more opaque than the gas used for inflating the balloon. In addition, increased visibility of the balloon can be obtained by inflating the balloon with a diluted radiopaque contrast solution. In addition, radiopaque bands of a suitable material such as platinum or a platinum-tungsten alloy can be placed on the proximal and distal balloon stems 81 and 82 to aid in ascertaining the position of the balloon. Similarly, radiopaque rods may be inserted in the distal balloon shaft tubing, in the control wire or balloon inflation lumens.

The intraluminal grafting apparatus also includes a control wire assembly 54, which is shown in FIGS. 1 and 4. The distal end of the control wire assembly consists of a distal capsule assembly 90. As shown in more detail in FIGS. 9–14, the distal capsule assembly comprises a control wire 91 secured within a distal cap 92. A hollow distal capsule 93 is secured to the distal cap and coaxially surrounds the control wire.

The control wire 91 is threaded through aperture 94 in the balloon catheter shaft 61 and is slidably disposed in the balloon catheter shaft lumen 65. Distal end 95 of the control wire is embedded in distal cap insert 96 which is secured to the distal cap 92 by means of an adhesive, solvent bonding, ultrasonic welding or by heat shrinking. As shown in FIG. 9, the distal cap insert is formed with radiopaque markers 97 and 98. Preferably, a 0.04 inch (1.01 mm) wide, 0.005 inch (0.127 mm) thick and 2 millimeters long ribbon is disposed in slots formed in the circumference of the insert at a 90 degree angle from the control wire.

As shown in FIG. 10, balloon catheter proximal cap 100 is secured to the balloon catheter shaft 61 at a position distal the balloon distal stem 82 and proximal the aperture 95. The proximal cap is secured to the balloon catheter shaft by adhesive and by means of a retaining bump 101. Retaining sleeve 102 slidably secures the control wire 91 against the balloon catheter shaft. Thus, as the control wire is moved in a longitudinal manner, the distal end of the control wire 95, distal cap insert 96, the distal cap 92 and distal capsule 93 each move as a single assembly. The proximal edges 103 of the distal capsule are rolled, curved or crimped inward so that the proximal cap will lock into the distal capsule when the distal capsule is advanced.

Referring to FIG. 11, the distal cap 92 may be formed from polycarbonate or other suitable material for insertion through the body lumen. The distal cap is formed with a bore 104 of approximately the same diameter as the outer diameter of balloon catheter shaft 61. Similarly, the distal cap insert 96 may be formed of the same material as the distal cap, wherein the distal cap insert is provided with a bore 105 for receiving the balloon catheter shaft. The distal cap is further provided with a recess 106 or other means for receiving the distal end of the distal capsule 93. The distal capsule is preferably formed of stainless steel, but may be formed of other suitable biocompatable material, such as a nickel titanium. The distal cap recess is angled to allow crimping of the distal capsule to the distal cap.

The outside diameter of the distal cap 92 and capsule 93 may range from 4 to 9 millimeters and is preferably 0.282 inches (7.16 mm) in outer diameter and 0.276 inches (7.01 mm) inner diameter. Similarly, the balloon catheter proximal cap 100 outer diameter is comprised of stainless steel and has an outside diameter slightly less that of the distal capsule so as to provide a smooth transition. The proximal end of the proximal cap is preferably rounded to minimize trauma in the vessel and to facilitate balloon retraction into the graft 55 during the emplacement process. The distal capsule may range in length from one to five centimeters, and preferably is three centimeters long so as to adequately retain the distal end of the graft 55.

FIGS. 12-14 show an alternative and embodiment of the distal cap assembly 90. In this embodiment, the core wire 91 is threaded through an opening 107 in the distal cap insert 108. A longitudinal slot 109 is cut out in the balloon catheter shaft 61 to expose the core wire lumen 65. The control wire is formed in a U-shaped bend over the opening in the distal cap insert and is configured to slide within the slot and the core wire lumen of the balloon catheter shaft. The distal end of the control wire resides in the portion of the core wire lumen beyond the end of the slot. This configuration allows the distal cap assembly to move axially along the balloon catheter shaft. The U-shaped bend of the control wire through the distal cap insert, however, prevents the distal cap assembly from rotating in relation to the balloon catheter shaft. As described above, the balloon catheter insert is firmly secured within the distal cap. To prevent rotation of the distal cap, a three centimeter length of the control wire extends distal of the distal cap and is slidably disposed in the balloon catheter shaft lumen 65.

As shown in FIGS. 15-17, a handle assembly 110 is secured to the proximal end of the control wire 91. The handle assembly comprises a proximal body 111, a distal body 112, a control knob 113 with threaded shaft 114 and a guiding member 115. The two handle body parts have a central bore for receiving the balloon catheter shaft 61. The guiding member is coaxially disposed over the balloon catheter shaft and extends distally from the central bore in the distal handle body. The proximal end of the guiding member is secured to the balloon catheter shaft approximately one centimeter proximal from the distal end of the distal handle body by means of a polyethylene sealing tube 116 which is heat shrunk over the proximal end of the guiding member. An adhesive may be used to fix the distal handle body to the guiding member.

Guiding member 115 consists of a rigid thin wall tube formed of a suitable material such as stainless steel, e.g., a catheter hypotube. The guiding member has a length of about 45 centimeters and has an outside diameter of 0.095 inches (2.41 mm) and an inside diameter of 0.087 inches (2.21 mm). The control wire 91 preferably consists of an elongate solid flexible stainless steel wire having a FEP or lubricating coating. The coated control wire is about 0.02 inches (0.508 mm) in diameter so as to provide sufficient strength to move the distal capsule assembly 90 without breaking or kinking. Referring to FIG. 15, the control wire resides in the balloon catheter lumen 65 and extends from the distal capsule assembly to an aperture 117 located in the lumen just proximal of the proximal end of the guiding member.

The proximal end of the control wire 91 is disposed within a longitudinal central bore in a retaining tube 120 approximately six centimeters long. The retaining tube's proximal end is slidably disposed within a longitudinal guiding slot 121 in proximal handle body 111. Similarly, the retaining tube's distal end is slidably disposed within an longitudinal upper slot 122 in the distal handle body 112. A transverse threaded bore 123 is located approximately 0.25 inches (6.35 mm) from the proximal end of the retaining tube for receiving the threaded shaft 114. The threaded shaft is turned down in the threaded bore to engage the control wire to secure the control wire firmly in the retaining tube.

The threaded shaft 114 extends upwardly from the retaining tube 120 through the proximal handle body 111 and is movable within the guiding slot 121. The control knob 113 is threaded onto the threaded shaft, wherein the control knob can be turned down and tightened onto the proximal handle body, thereby locking the retaining tube and control wire 91 in a fixed position relative to the balloon catheter. When the control knob is loosened, any longitudinal movement of the control knob causes corresponding movement of the distal capsule assembly 90.

As shown in FIGS. 1 and 5, the capsule catheter assembly 52 consists of a proximal capsule catheter assembly 130 secured to the distal end of a flexible elongate tubular member 131 formed of a suitable plastic material such as polyether block amide available under the trademark "PEBAX", available from Atochem Polymers, Glen Rock, N.J. The capsule catheter elongate tubular member is of a suitable length as, for example, 40 to 100 centimeters and preferably approximately 60 centimeters for the abdominal aortic artery and approximately 80 centimeters for the thoracic aortic artery. The elongate tubular member has a preferred outside diameter of 0.187 inches (4.75 mm) and an inside diameter of 0.125 inches (3.175 mm). The elongate tubular member can be produced in a certain color such as blue. To render the elongate tubular member radiopaque under x-rays, its material of construction may contain a radiopaque material, such as twenty percent by weight of bismuth subcarbonate or barium sulfate. The elongate tubular member may have markings or bands distal of the wye adapter 145 at predetermined positions to indicate capsule jacket retraction and locking points.

The proximal catheter assembly 130 has a proximal capsule 132 mounted on the distal extremity of the capsule catheter elongate tubular member 131. The proximal capsule has a preferred diameter ranging from four to nine millimeters, which may be configured to accommodate different size grafts. The proximal capsule is configured to match the size of the distal capsule assembly 90. Thus, the proximal capsule is preferably made of stainless steel or similar impermeable and rigid, or semi-flexible material. The elongate tubular member also serves as a shaft for advancing the proximal capsule, as hereinafter described. Thus, the elongate tubular member should have a diameter which is less than that of the proximal capsule, preferably having an outside diameter ranging from three to seven millimeters.

Referring to FIG. 8, the proximal capsule 132 is secured to the distal extremity of the elongate tubular member 131 by means of a capsule adapter assembly 133. The capsule adapter assembly comprises a housing 134 and an inner sleeve 135, which may be constructed from polycarbonate. The capsule adapter housing distal extremity 136 is secured in the proximal extremity of the capsule, for example, by crimping, by using a press fit swaging or an adhesive such as a cyanoacrylate ester. The capsule adapter housing distal extremity may be angled to facilitate securing the housing to the proximal capsule.

The proximal extremity of the capsule adapter housing 134 is secured to the distal extremity of the elongate tubular member 131 by means of an cyanoacrylate ester adhesive, or other suitable means. To facilitate a mechanical lock, the elongate tubular member distal extremity is molded to form a flange 137, wherein the capsule adapter housing is configured so as to close around the flange. The capsule adapter housing is further provided with a recess for receiving the capsule adapter inner sleeve 135. The inner sleeve is provided with a bore of a suitable diameter so as to allow the balloon catheter shaft 61 to reside therein. The inner sleeve may further be provided with radiopaque marker rods or flat ribbon 138 for detection of the capsule adapter assembly 130 during fluoroscopy.

A wye adapter 145 is secured to the proximal extremity of the flexible tubular member 131 of the capsule catheter. The central arm 146 of the wye adapter is connected to a Touhy Borst adapter 147 which tightens around the guiding member 115 disposed in the central arm of the wye adapter. The side arm 148 of the wye adapter has a stop cock 149 mounted therein which is movable between open and closed positions. The stop cock is provided with a Luer fitting 150 which is configured to accept a syringe for injecting a dye. Air may be purged from the capsule jacket assembly 53 by injecting fluid through the Luer fitting. The injection fluid will exit purge ports 151 and 152, thereby filling the capsule jacket assembly with injection fluid. The Luer fitting may be attached to a saline drip line during the operative procedure.

Referring to FIGS. 1, 6 and 8, the capsule jacket assembly 53 is slidably disposed coaxially over the capsule catheter assembly 52 and the balloon catheter assembly 51. The capsule jacket assembly is comprised of a main sheath 160, a capsule jacket support sheath 161 and a locking connector 162. The main and support sheaths are coaxial from their proximal end, to a point approximately 15 centimeters from the distal end 163 of the main sheath, depending on the length of the graft. At the point where the support sheath terminates, the main sheath flares to an expanded diameter to cover the proximal capsule 132 and the distal capsule 93. The diameter of the main sheath is about 0.263 inches (6.68 mm) at its proximal end and about 0.3 inches (7.62 mm) at the distal end 163. The proximal ends of the sheaths may be secured to the sheath adapter 164 of the locking connector by mechanical means and by adhesive. The distal end of the main sheath of the capsule jacket is provided with radiopaque marker 166.

When the capsule jacket assembly 53 is in its most distal position, the distal end 163 of the capsule jacket main sheath extends to cover at least a portion of the distal capsule assembly 90. Similarly, the capsule jacket locking connector 162 is thereby positioned just proximal the proximal capsule catheter purge port 151. Prior to insetion into the lumen, locking ring 165 is turned down to hold the capsule jacket assembly firmly in place, thereby maintaining a smooth transition surface along the length of the intraluminal grafting system 50 which resides in the body vessels. When the locking ring is released, the capsule jacket assembly may be moved to a furthermost proximal position, wherein at least a portion of the proximal capsule catheter assembly is exposed. Thus, the locking connector is positioned just distal the capsule catheter wye adapter 145. The locking ring may be tightened at any intermediate position to firmly secure the capsule jacket assembly at the desired location. In addition, a radiopaque marker 166 is provided at the distal end of the main sheath to facilitate proper linear positioning of the main sheath.

As shown in FIGS. 1 and 7, the intraluminal grafting apparatus 50 also includes an expandable intraluminal vascular graft 55 for implanting in a body vessel. Referring to FIG. 23, the graft consists of a deformable tubular member 170 which is provided with superior end 171, inferior end 172 and a cylindrical or continuous wall 173 extending between the superior and inferior ends of the graft. The tubular member may have a length in the range of 8 to 20 centimeters, where 10 centimeters is suitable for most patients. The tubular member may have a maximum expandable diameter ranging from 14 to 40 millimeters and a minimum diameter in a collapsed condition of 0.175 to 0.3 inches (4.44–7.62 mm). The continuous wall can be woven of any surgical implantable material such as polytetrafluoroethylene or a polyester fiber made from polyethylene terephthalate (PET), such as "DACRON" type 56. One material found to be satisfactory is "DEBAKEY" soft woven "DACRON" vascular prosthesis (uncrimped) sold by C. R. Bard of Billerica, Mass. In order to prevent unraveling of the woven material at the ends, the ends can be melted with heat to provide a small melted bead of material on each end.

Referring to FIG. 23, expandable attachment means 175 is secured adjacent the superior end 171 of the tubular member 170. Similarly, expandable attachment system 176 is secured adjacent the tubular member's inferior end 172. Each attachment system serves to yieldably urge the tubular member from a first compressed or collapsed position to a second expanded position. Each attachment system is formed of a plurality of vees 177 with the outer apices 178 and inner apices 179 of the vees being formed with helical coil springs 180 to yieldably urge the long legs 181 and short legs 182 of each of the vees outwardly at a direction approximately at right angles to the plane in which each of the vees lie.

As shown in more detail in FIG. 25, the superior attachment system 175 is comprised of a single piece of wire which is formed to provide the vees 177 and also to define the helical coil springs 180 between the legs 181 and 182.

The two ends of the single piece of wire can be welded together in one of the legs to provide a continuous spring-like attachment means. In the construction shown in FIG. 23, it can be seen that the attachment means have apices lying in four longitudinally spaced-apart parallel planes which are spaced with respect to the longitudinal axis of the tubular member 170.

The superior and inferior attachment means 175 and 176 are secured to the superior and inferior ends 171 and 172, respectively, of the tubular member 170 by suitable means such as a polyester suture material 190. As shown in FIG. 23, the suture material is used for sewing the attachment means onto the wall 173 of the tubular member. Knots 191 are preferably formed on each of the legs or struts 181 and 182 to firmly secure each leg to the graft. The legs may be secured so that the apices lying in each plane are staggered to provide for the minimum profile when the attachment means is placed in its collapsed condition. The inferior attachment means 176 may be attached to the inferior end of the graft 172 in a similar manner.

As shown in FIGS. 25 and 26, wall engaging members 195 and 196 are preferably secured to the legs 181 and 182 in the vicinity of the outer apices 178 by suitable means such as welding. The wall engaging members have a diameter ranging from 0.01 to 0.018 inches (0.254–0.457 mm) and a length from 0.5 to 5.0 millimeters. The wall engaging members are preferably sharpened to provide conical tips, and should have a length which is sufficient for the tip to penetrate into and perhaps through the corporeal lumen wall.

The superior attachment means 175 and the wall engaging members 195 secured thereto are formed of a corrosion resistant material which has good spring and fatigue characteristics. One such material found to be particularly satisfactory is "ELGILOY" which is a cobalt-chromium-nickel alloy manufactured and sold by Elgiloy of Elgin, Ill. The wire can have a diameter ranging from 0.008 to 0.016 inches (0.203–0.406 mm), with a smaller diameter wire being utilized for the smaller diameter grafts. For example, 0.012 to 0.016 inch (0.305–0.406 mm) diameter wire for the frame and wall engaging members may be used in the larger grafts of eighteen to twenty-eight millimeters diameter, and 0.008 to 0.012 inch (0.203–0.305 mm) diameter wire may be used in the smaller grafts being eight to sixteen millimeters in diameter.

It has been found that the spring force created by the helical coils 180 at the apices 178 and 179 is largely determined by the diameter of the wire. The greater the diameter of the wire, the greater the spring force applied to the legs 181 and 182 of the vees. Also, the longer the distances are between the apices, the smaller the spring force that is applied to the legs. It therefore has been desirable to provide a spacing between the outer extremities of the legs of approximately one centimeter, although smaller or larger distances may be utilized.

To facilitate securing the graft 55 in the corporeal lumen, the wall engaging members 195 and 196 of the superior attachment means 175 and inferior attachment means 176 may be angled with respect to longitudinal axis of the tubular member 170. The wall engaging members face outwardly from the tubular member to facilitate holding the graft in place. Preferably, the wall engaging members on the superior attachment means are inclined from the longitudinal axis and toward the inferior end of the graft 172 by 55° to 85° and preferably about 75°. Likewise, the wall engaging members of the inferior attachment means may be inclined towards the superior end of the graft 175 by 30° to 90° and preferably 85°. By angling the wall engaging members so that they resist the force of the blood flow, the implanted wall engaging members oppose migration of the graft.

The helical coil springs 180 placed at the apices 178 and 179 serve to facilitate compression of the graft 55 to place the superior and inferior attachment means 175 and 176 within the capsule assemblies 90 and 130, as hereinafter described. The compression of the graft is accomplished by deformation of the coil springs within their elastic limits. Placing the apices in different planes and staggering or offsetting the wall engaging members 195 and 196 significantly reduces the minimum compressed size of the graft. Having the apices in different planes also helps to prevent the wall engaging members from becoming entangled with each other. The natural spring forces of the helical coil springs serves to expand the graft to its expanded position as soon as the attachment means is free of the capsule means.

The graft 55 preferably contains radiopaque marker means for locating the graft and for detecting any twisting of the graft during deployment. The radiopaque marker means takes the form of two sets of radiopaque markers 197 and 198. The radiopaque markers are made of a suitable material such as a platinum tungsten alloy wire of a suitable diameter such as 0.004 inches (0.102 mm) which is wound into a spring coil having a diameter of 0.04 inches (0.102 mm). The radiopaque markers are secured to the tubular member 170 by sutures 199, using the same material sued to secure the attachment means to the graft.

As shown in FIG. 23, the radiopaque markers 197 and 198 are located on the tubular member 170 of the graft 55 in a line parallel to the longitudinal axis of the tubular member. Each tubular member preferably has at least two sets of markers such that the first marker is positioned 0.5 centimeters from the superior attachment system 175. Additional markers are positioned every one centimeter thereafter for the length of the tubular member. The last marker in each set is 0.5 centimeters away from the inferior attachment system 176. Thus, the total number of markers in each set depends upon the length of the graft.

Referring also to FIG. 24, each of the first set of radiopaque markers 197 has a preferred length of 3 millimeters. Each of the second set of markers 198 preferably has a smaller length, for example 2 millimeters, and are positioned along the longitudinal axis of the tubular member 170 at a position 180° from the first set of markers. By placing markers of different lengths along the axis of the tubular member, it is possible to ascertain the position of the graft 55 and to determine whether the graft has twisted between its superior and inferior ends 171, 172. Under fluoroscopy, the two sets markers will be exhibited as two relatively straight lines for an untwisted graft, wherein a twisted graft will be revealed by a non-linear pattern of markers. By placing the markers at equal increments apart, it is possible to use fluoroscopy to ascertain longitudinal compression or tension on the graft.

The sizing of the graft 55 may be performed on a patient-by-patient basis, or a series of sizes may be manufactured to adapt to most patient needs. For the repair of an aortic aneurism, the length of the graft is selected so to span approximately one centimeter superior and one centimeter inferior of the aneurysm, wherein the wall engaging members 195 and 196 of the graft can seat within normal tissue of the vessel on both sides of the aneurysm. Thus, the graft should be about two centimeters longer than the aneurysm being repaired. During the preimplant fluoroscopy procedure, a conventional pigtail catheter is used to determine the locations of the renal arteries to ensure the renals will not be covered by the implanted graft. Similarly, the diameter of the tubular member 170 is selected by measuring the corporeal lumen which will receive the graft by conventional radiographic techniques and then selecting a tubular member having a diameter one millimeter larger than that measured.

FIG. 8 depicts the distal end of the intraluminal grafting system 50 assembled for deployment. The graft 55 is disposed within the proximal capsule assembly 130, the distal capsule assembly 90 and the capsule jacket assembly 53. The superior end of the graft 171 and superior attachment means 175 are removably retained within the distal capsule 93. Likewise, the inferior end of the graft 172 and inferior attachment means 176 are removably retained within the proximal capsule 132. The distal cap 92 is in its retracted or proximal position adjacent to proximal cap 100. Similarly, core wire 91 is locked via control knob 113 in its retracted or proximal position. During initial deployment, capsule catheter tubular member 131 is in its most distal position in relation to balloon catheter assembly 51 and is locked in place by the locking ring on the Touhy Borst adapter 147.

During initial deployment, the distal end of the balloon catheter 80 is positioned such that the balloon 60 resides within the tubular member 170 of the graft 55, as shown in FIG. 8. The proximal cap 100 is positioned just proximal the distal cap 92 and is disposed within the distal capsule 93. Likewise, pusher button 85 is disposed just proximal the inferior attachment means 176 of the graft. The capsule jacket assembly 53 is positioned such that the distal end of the capsule jacket main sheath 160 overlaps at least a portion of the distal capsule 93. During deployment, capsule jacket locking connector 162 secures the main sheath in place. Thus, when any movement or force is applied to the handle assembly 110, the entire apparatus 50 moves as a single unit.

By way of example, the following describes a method of repair of an aortic aneurism using the method comprising the present invention for intraluminal placement of a graft in an aorta. First, a patient is prepared in a conventional manner by use of a guide wire 56, a dilator and sheath (not shown) to open the femoral artery or vessel of the patient. The distal end of the intraluminal grafting apparatus 50 is then inserted into the sheath, which has previously been placed in the femoral artery. In the preferred embodiment of the present invention, balloon catheter lumen 63 is provided for receiving the guide wire 56. However, the following procedure may also be used when the guiding member is constructed as part of the balloon catheter.

As shown in FIG. 27, the guide wire 56 is introduced by the physician into the femoral artery and advanced to the desired location in the aorta 200 and adjacent to the diseased or damaged portion of the vessel 201. The balloon catheter assembly 51, the capsule catheter assembly 52, the capsule jacket assembly 53 and the control wire assembly 54 are all configured for deployment as shown in FIGS. 1 and 8. Thus, the assemblies are advanced by the physician as a single unit over the guide wire. The physician uses the handle assembly 110 and the proximal end of the balloon catheter 70 to guide the distal end of the assemblies over the guide wire. Typically, the desired position for implanting the graft 55 will be within the abdominal aorta with the superior extremity 171 of the graft at least one centimeter inferior to the lower renal artery.

When the distal capsule assembly 90 and the superior attachment means 175 are in the desired position, the superior end of the graft 55 is implanted. First, the locking ring 165 of the capsule jacket assembly 53 is loosened to allow movement of the capsule jacket main sheath 160. While using one hand to firmly grasp the capsule catheter assembly 52 and hold it stationary, the physician grasps the sheath adapter 164 with the other hand and gently pulls the sheath adapter proximally towards the capsule catheter wye adapter 145, as shown in FIG. 28. The capsule jacket assembly is moved about 6 centimeters to fully expose the distal capsule assembly, and partially expose the graft. The locking ring is then tightened to hold the capsule jacket assembly in place.

At this point in the procedure, the superior end of the graft 171 is disposed in the distal capsule 93, the inferior end of the graft 172 is securely retained with in the proximal capsule 132 and the distal end of the capsule jacket main sheath 160 is located about midway between the ends of the graft. The control knob 113 is then loosened to permit relative movement between the distal capsule assembly 90 and the balloon catheter assembly 51 to expose superior end 171 of the graft 55. Again using one hand to firmly grasp the handle assembly 110, the physician slides the control knob distally toward the wye adapter 145. Since the distal cap 92 and distal capsule 93 are secured to the control wire 91, they move in a about a 1:1 ratio with the movement of the control knob. The control knob is moved distally approximately 3 centimeters, which moves the distal capsule from engagement with the superior attachment means 175 and exposes the balloon catheter proximal cap 100. The control knob is then locked in place. As soon as the distal capsule has cleared the superior attachment means 175, the superior extremity of graft expands outwardly under the force of the self-expanding attachment means which springs into engagement with the vessel wall 202.

Once the superior attachment means 175 is exposed, steps are taken to firmly seat or urge the wall engaging members 195 an 196 in the vessel lumen. First, locking ring 165 is loosened, and the capsule jacket assembly 53 is moved proximally to a point where the distal end of the main sheath 160 is positioned just proximal the distal end of the proximal capsule 132 (FIG. 29). The capsule jacket assembly is then locked in place. Then, the locking ring on the capsule catheter Touhy Borst adapter 147 is loosened to permit relative movement between the capsule catheter assembly 52 and the balloon catheter 51. While the physician uses one hand to hold the capsule catheter assembly stationary, the handle assembly 110 is grasped by the other hand and pushed distally to position the center of the balloon 60 into the superior extremity of the graft 171. The radiopaque marker 84 is used to align the balloon and attachment means.

Thereafter, a conventional hand operated syringe or inflation assembly (not shown) is attached to the balloon catheter inflation port 74. The balloon is then expanded by introducing a suitable gas such as carbon dioxide or a dilute radiopaque liquid from the syringe to urge the wall engaging members 195 and 196 outwardly to firmly emplace the attachment system within the vessel wall 202. The balloon may be deflated and inflated repeatedly to ensure the superior attachment means is firmly implanted in the vessel. The balloon may be then deflated or may remain in an inflated position during the next steps of the procedure.

As shown in FIG. 30, the next step is to implant or anchor the inferior attachment system 176. With the handle assembly 110 held firmly in place, the capsule catheter assembly 52 is moved proximally until the inferior attachment system and inferior end of the graft 172 are completely clear of the proximal capsule 132. Once the inferior extremity of the graft is free of the proximal capsule, the inferior attachment system will spring open and the wall engaging members 195 and 196 will engage the vessel wall 202. Leaving the balloon 60 inflated while the capsule catheter assembly is moved ensures that the superior attachment system 175 will remain firmly secured in place. Thereafter, the balloon may be deflated and the capsule catheter locking ring 147 secured to the guiding member 115, thereby securing the capsule catheter assembly 52 to the balloon catheter assembly 51.

In certain circumstances, an alternate method of deploying the inferior attachment system 176 may be employed. Such an alternate method may be advantageous when a graft has been chosen that is of a length which exceeds the length of the aorta, thereby jeopardizing a secure emplacement of the inferior extremity of the graft. In such cases, the balloon 60 is deflated so that the balloon catheter assembly 51 can be freely moved within the corporeal lumen. Next, the capsule catheter assembly 52 is advanced in a distal direction so that the inferior attachment system is positioned in the desired location of the aorta 200.

With the inferior attachment system 176 and the inferior extremity of the graft 172 in the portion of the corporeal lumen where the wall engaging members 196 are to engage the vessel wall 202, the balloon catheter shaft 61 is advanced so that the pusher button 85 and retaining bump 86 engage the inferior attachment system. Then the user holds the handle assembly 54 and balloon catheter assembly 51 fixed while moving the capsule catheter assembly 52 in a proximal direction. When the proximal capsule assembly 130 moves sufficiently distally, the inferior attachment system will be released from the proximal capsule 132. The inferior attachment system and inferior wall engaging members may then be secured with the balloon 60.

As shown in FIG. 31, the handle assembly 110 is moved proximally so that the balloon 60 is then retracted further into the graft 55 and placed adjacent the inferior attachment system 176. Again, the balloon radiopaque marker 84 is used to align the center of the balloon with the attachment means. The balloon is then inflated, and perhaps deflated and inflated, to expand the attachment system and ensure that the wall engaging members 195 and 196 are firmly urged and implanted in the vessel wall 202. Thereafter, the balloon is finally deflated.

As shown in FIG. 32, the proximal capsule assembly 130 and balloon 60 are moved proximal the graft 55. First the locking ring 147 is loosened. Then, while holding the capsule catheter assembly 52 in place by grasping the wye adapter 145 with one hand, the balloon catheter assembly 51 is moved proximally by gently pulling the handle assembly 110 with the other hand. Thus, the capsule catheter assembly and balloon catheter are in the same relative position as they were just prior to deployment (FIG. 8). Also, the proximal end 103 of the distal capsule 93 has been mated with the proximal cap 100 for smooth transition.

Finally, as shown in FIG. 33, the capsule jacket locking ring 165 is loosened. While holding the capsule jacket sheath adapter 164 in place, the balloon catheter and capsule catheter assemblies 51 and 52 are moved proximally and in unison by gently pulling the wye 145 of the capsule catheter assembly. The catheter assemblies are moved until the distal end of the main sheath 163 covers the distal capsule 93 or until the proximal capsule adapter housing 134 mates with the flared transition of the capsule jacket, thereby creating a smooth transition along the entire length of the intraluminal grafting apparatus 50. Thereafter, the balloon catheter assembly, capsule catheter assembly, capsule jacket assembly 53 and control wire assembly 54 are removed from the aorta through the femoral artery. The graft 50 and attachment means 175 and 176 remain secured to the vessel wall 202, thereby sealing the aneurism 201 from blood flow.

The entire procedure described herein can be observed under fluoroscopy. The relative positioning of the graft 55 and the balloon 60 can be readily ascertained by the radiopaque attachment systems 175 and 176, radiopaque markers 197 and 198 provided on the graft, and the radiopaque marker 84 on the balloon shaft 61. If any twisting of the graft has occurred between placement of the superior attachment system and the inferior attachment system, then the twisting can be readily ascertained by observing the series of markers 197 and 198. Adjustments to eliminate any twisting which may have occurred can be made before exposing the graft's inferior extremity 172 by rotation of the capsule catheter assembly 52. Any excessive graft compression can be ascertained by observing the radiopaque markers 197 and 198 under fluoroscopy. Adjustments to eliminate graft compression can be made before exposing the inferior extremity of the graft by applying tension on the capsule catheter assembly 52.

Post implant fluoroscopy procedures can be utilized to confirm the proper implantation of the device by the use of a conventional pigtail catheter or by injecting dye into the guide wire lumen of the balloon catheter shaft. Thereafter the sheath can be removed from the femoral artery and the femoral artery closed with conventional suturing techniques. Tissues should begin to grow into the graft within two to four weeks with tissue completely covering the interior side of the graft within six months so that no portion of the graft thereafter would be in communication with the blood circulating in the vessel. This establishes a complete repair of the aneurysm which had occurred.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. A system for placing a graft in a lumen formed by a wall in a body, said system comprising:
   a tubular graft having a superior extremity and an inferior extremity, said graft being deformable between a collapsed condition and an expanded condition;
   first anchoring means secured to the superior extremity of said graft for attaching the superior extremity of said graft to the lumen wall;
   second anchoring means secured to the inferior extremity of said graft for attaching the inferior extremity of said graft to the lumen wall;
   said first and second anchoring means each including a plurality of wall engaging members and a continuous wire frame configured to provide a plurality of vees;
   a distal capsule assembly for covering said first anchoring means;
   a proximal capsule assembly for covering said second anchoring means, wherein at least a portion of said graft between said first and second anchoring means remains uncovered;
   placement means for positioning said graft, said distal capsule assembly and said proximal capsule assembly at a desired location in the lumen, said placement means including means for moving said distal capsule assembly relative to said proximal capsule assembly to uncover said first anchoring means and means for moving said proximal capsule assembly relative to said graft to uncover said second anchoring means;

wherein said placement means includes first catheter means having a balloon secured to a flexible elongate shaft having an inflation lumen in fluid communication with the balloon, the first catheter means being capable of moving the balloon within said graft and into engagement with said first anchoring means and with said second anchoring means:

wherein said distal capsule assembly includes a distal capsule and a proximal cap slidably retained in the distal capsule and secured on the shaft of the first catheter means of said placement means, wherein the shaft extends through the proximal capsule assembly, the proximal cap, and the distal capsule: and a removable sleeve of a flexible material, said removable sleeve including a main sheath having an expanded diameter configured to extend over said proximal capsule assembly, said graft and at least a portion of said distal capsule assembly, wherein a smooth transition is provided between said distal capsule assembly and said proximal capsule assembly.

2. The system as recited in claim 1, wherein said placement means includes means for moving said proximal capsule assembly to uncover said second anchoring means before said distal capsule assembly is moved to uncover said first anchoring means.

3. The system as recited in claim 1, wherein said removable sleeve further comprising means for securing said removable sleeve to said placement means and for manipulating said removable sleeve to uncover said distal capsule assembly and to uncover said proximal capsule assembly.

4. The system as recited in claim 1, wherein the placement means further comprises a control wire having a proximal end and a distal end secured to the distal capsule, the shaft of the first catheter means of said placement means being provided with a control wire lumen for slidably retaining the control wire, whereby the distal capsule moves relative to the shaft by movement of the proximal end of the control wire.

5. The system as recited in claim 4, wherein said placement means further comprises second catheter means including a flexible elongate shaft having a proximal end positioned distal the proximal end of the shaft of said first catheter means and having a distal end secured to the proximal capsule assembly, such that movement of said second catheter means may move said proximal capsule assembly without moving said distal capsule assembly.

6. The system as in recited claim 5, wherein the shaft of the first catheter means of said placement means is coaxially disposed within the shaft of the second catheter means of said placement means, said removable sleeve being coaxially disposed over both the shaft of the first catheter means and the shaft of the second catheter means.

7. The system as recited in claim 6, further comprising a guide wire, wherein the shaft of the first catheter means of said placement means is further provided with a guide wire lumen extending the length of the shaft for retaining said guide wire.

* * * * *